United States Patent [19]

Zipplies et al.

[11] Patent Number: 4,945,112
[45] Date of Patent: Jul. 31, 1990

[54] GUANIDINIUM COMPOUNDS AND FUNGICIDES CONTAINING THEM

[75] Inventors: Matthias Zipplies, Hirschberg; Hubert Sauter, Mannheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 324,422

[22] Filed: Mar. 16, 1989

[30] Foreign Application Priority Data

Apr. 19, 1988 [DE] Fed. Rep. of Germany ....... 3812945

[51] Int. Cl.$^5$ ................... A01N 31/08; A01N 33/04; C07C 87/24; C07C 143/34
[52] U.S. Cl. ........................................ 514/555; 562/45
[58] Field of Search ............................ 562/45; 514/555

[56] References Cited

U.S. PATENT DOCUMENTS 4,659,739  4/1987  Yoshioka et al. .................... 514/555
4,694,086  9/1987  Morimoto et al. .................. 564/236

FOREIGN PATENT DOCUMENTS 1114155  5/1968  United Kingdom .
1294443  10/1972  United Kingdom .

OTHER PUBLICATIONS

Chemical Abstracts, 10th Collective Index, C15H35N9.
Chemical Abstracts, 89:158758a, "Guanidine Organic Salts Microbiocides", (1978).

Primary Examiner—J. E. Evans
Attorney, Agent, or Firm—Oblon, Spivak, McClelland, Maier & Neustadt

[57] ABSTRACT

Guanidiniumdodecylbenzene sulfonates of the formula

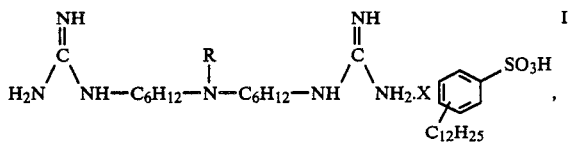

where
R is the group —H, —CH$_3$ or

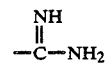

and
X is 1, 2, 3 or 4, and fungicides containing these compounds.

10 Claims, No Drawings

GUANIDINIUM COMPOUNDS AND FUNGICIDES CONTAINING THEM

The present invention relates to dodecylbenzene sulfonates of guanidino-substituted bis-(6-aminohexyl)-amine, their use as fungicides, fungicides containing these compounds, and methods of combating fungi with these compounds.

The compound

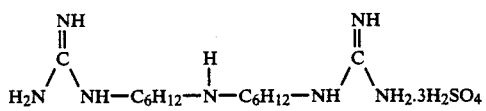

and its fungicidal action are known from GB No. 1,114,155.

However, the compound has in practice an unsatisfactory fungicidal action on plant-pathogenic fungi. Further, it has a strong phytotoxic action on crop plants.

EP No. 155 509 discloses the compound

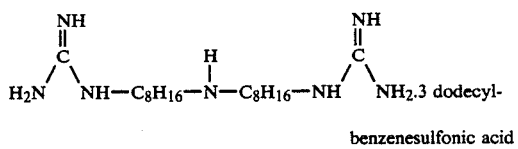

and its fungicidal action.

This compound is somewhat better tolerated by crop plants, but is only very sparingly soluble in water.

The object of the invention was therefore to reduce the damaging action of these compounds, to make them better soluble in water and thus to improve their use possibilities as fungicides in agriculture.

We have now found that the guanidine salts of dodecylbenzenesulfonic acid of the formula I

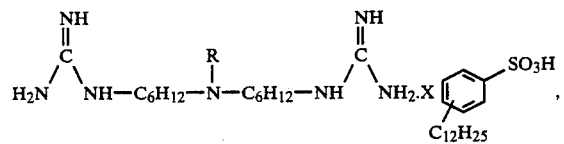

where
R is the group —H, —CH$_3$ or

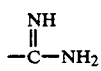

and
X is 1, 2, 3 or 4, are tolerated much better than the prior art compounds and have a good action on phytopathogenic fungi. The reduced phytotoxicity of the compounds according to the invention enables them to be used for combating injurious fungi in sensitive crops, for example scab (*Venturia inaequalis*) and mildew (*Podosphaera leucotricha*) in apples, and powdery mildew (*Uncinula necator*) and rot (*Botrytis cinerea*) in grapes.

By "dodecylbenzenesulfonic acid", we mean not only the pure acid, but also the commercial isomer mixture. The isomer mixture may also contain slight amounts of homologous compounds which contain, instead of the dodecyl radical, a longer or shorter alkyl radical.

Examples of fungicidal guanidine compounds according to the invention which are tolerated by plants are N,N'''-(iminodi-6,1-hexanediyl)-bisguanidine-tris-dodecylbenzene sulfonate of the formula II and N,N'''-bis[6(aminoiminomethyl)-amino]-hexylguanidine-tris-dodecylbenzene sulfonate of the formula III (hexyl=n-hexyl):

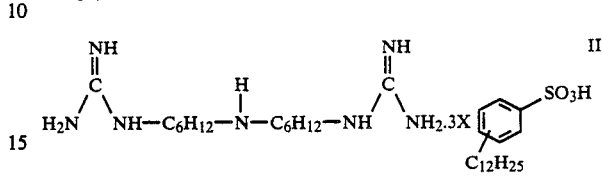

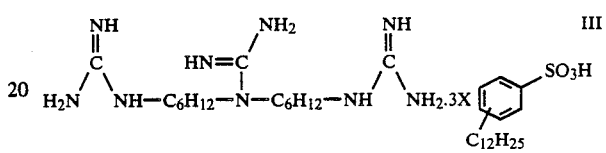

The compounds according to the invention may be prepared for instance by reacting a solution of an acid addition salt consisting of guanidino-substituted bis-(6-aminohexyl)-amine and an inorganic or low-molecular-weight organic acid such as hydrochloric acid, sulfuric acid, phosphoric acid, carbonic acid, formic acid, acetic acid, propionic acid and oxalic acid with from 1 to 4 equivalents of dodecylbenzenesulfonic acid in a solvent such as water, methanol, ethanol, isopropanol and acetone, or mixtures thereof, at from 20° to 120° C., and isolating the reaction product for example by concentration, cooling or precipitation.

Preferred acid addition salts are the carbonates.

The compounds according to the invention may also be prepared by allowing a solution of one of the above-mentioned acid addition salts to react with an anion exchanger resin, and reacting the free guanidine derivative formed with from 1 to 4 equivalents of dodecylbenzenesulfonic acid in a solvent such as water, methanol or ethanol.

Advantageously, the compounds may also be manufactured for instance by reacting bis-(6-aminohexyl)-amine with from 2 to 4 equivalents of cyanamide and from 1 to 4 equivalents of dodecylbenzenesulfonic acid in a solvent such as water, methanol, ethanol and isopropanol, or mixtures thereof, at from 20° to 90° C. and a pH of from 3 to 10.

The following example illustrates the manufacture of the compounds according to the invention.

EXAMPLE 1

N,N'''-(iminodi-6,1-hexanediyl)-bis-guanidine-tris-dodecylbenzene sulfonate (compound II)

At 70° C., a solution of 170 g of sodium carbonate in 340 ml of hot water is added to 100 g of N,N'''-(iminodi-6,1-hexanediyl)-bis-guanidine sulfate (British No. 1,114,155) dissolved in 500 ml of water. The mixture is cooled with ice and filtered. The residue is dried under reduced pressure. There is obtained 53 g of N,N'''-(iminodi-6,1-hexanediyl)-bis-guanidine sesquicarbonate of melting point 171°–175° C.

15 g of the sesquicarbonate is dissolved hot in 100 ml of methanol; 37.5 g of dodecylbenzenesulfonic acid (isomer mixture) is added and stirring is continued until no more $CO_2$ evolves. The solvent is evaporated completely under reduced pressure. There is obtained 52.5 g of the title compound II in the form of a viscous resin.

1H-NMR ($CD_3OD$): δ=7.8–7.7 (m,6H); 7.3–7.18 (m,6H); 3.17 (t,4H); 2.98 (t,4H); 1.8–0.7 (m,91H).

IR (film): 3341, 3181, 2956, 2924, 2854, 1671, 1215, 1188, 1125, 1036 $cm^{-1}$.

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

*Erysiphe graminis* in cereals,

*Erysiphe cichoracearum* and *Sphaerotheca fuliginea* in cucurbits,

*Podosphaera leucotricha* in apples,

*Uncinula necator* in vines,

*Venturia inaequalis* (scab) in apples,

Helminthosporium species in cereals,

*Septoria nodorum* in wheat,

*Botrytis cinerea* (gray mold) in strawberries and grapes,

*Cercospora arachidicola* in groundnuts,

*Pseudocercosporella herpotrichoides* in wheat and barley,

*Pyricularia oryzae* in rice,

Fusarium and Verticillium species in various plants,

Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., on *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. II is mixed with 10 parts by weight of N-methyl-α-pyrrolidone. A mixture is obtained which is suitable for application in the form of very fine drops.

II. 20 parts by weight of compound no. III is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. II is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. III is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. II is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. III is intimately mixed with 97 parts by weight of particulate kaolin. A dust is obtained containing 3% by weight of the active ingredient.

VII. 30 parts by weight of compound no. II is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. III is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. II is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:
  sulfur,
  dithiocarbamates and their derivatives, such as
  ferric dimethyldithiocarbamate,
  zinc dimethyldithiocarbamate,
  zinc ethylenebisdithiocarbamate,
  manganese ethylenebisdithiocarbamate,
  manganese zinc ethylenediaminebisdithiocarbamate,
  tetramethylthiuram disulfides,
  ammonia complex of zinc N,N'-ethylenebisdithiocarbamate,
  ammonia complex of zinc N,N'-propylenebisdithiocarbamate,
  zinc N,N'-propylenebisdithiocarbamate and N,N'-polypropylenebis(thiocarbamyl) disulfide;
  nitro derivatives, such as
  dinitro(1-methylheptyl)-phenyl crotonate,
  2-sec-butyl-4,6-dinitrophenyl 3,3-dimethylacrylate,
  2-sec-butyl-4,6-dinitrophenyl isopropylcarbonate and diisopropyl 5-nitroisophthalate;
  heterocyclic substances, such as
  2-heptadecylimidazol-2-yl acetate,
  2,4-dichloro-6-(o-chloroanilino)-s-triazine,
  0,0-diethyl phthalimidophosphonothioate,
  5-amino-1-[-bis-(dimethylamino)-phosphinyl]-3-phenyl-1,2,4-triazole,
  2,3-dicyano-1,4-dithioanthraquinone,
  2-thio-1,3-dithio[4,5-b]quinoxaline,
  methyl 1-(butylcarbamyl)-2-benzimidazolecarbamate,
  2-methoxycarbonylaminobenzimidazole,
  2-(fur-2-yl)-benzimidazole,
  2-(thiazol-4-yl)benzimidazole,
  N-(1,1,2,2-tetrachloroethylthio)-tetrahydrophthalimide,
  N-trichloromethylthiotetrahydrophthalimide,
  N-trichloromethylthiophthalimide,
  N-dichlorofluoromethylthio-N',N'-dimethyl-N-phenylsulfuric acid diamide,
  5-ethoxy-3-trichloromethyl-1,,2,3-thiadiazole,
  2-thiocyanatomethylthiobenzothiazole,
  1,4-dichloro-2,5-dimethoxybenzene,
  4-(2-chlorophenylhydrazono)-3-methyl-5-isoxazolone,
  2-thiopyridine 1-oxide,
  8-hydroxyquinoline and its copper salt,
  2,3-dihydro-5-carboxanilido-6-methyl-1,4-oxathiyne,
  2,3-dihydro-5-carboxanilido-6-methyl-1,4-dioxide,
  2-methyl-5,6-dihydro-4H-pyran-3-carboxanilide,
  2-methylfuran-3-carboxanilide,
  2,5-dimethylfuran-3-carboxanilide,
  2,4,5-trimethylfuran-3-carboxanilide,
  2,5-dimethyl-N-cyclohexylfuran-3-carboxamide,
  N-cyclohexyl-N-methoxy-2,5-diethylfuran-3-carboxamide,
  2-methylbenzanilide,
  2-iodobenzanilide,
  N-formyl-N-morpholine-2,2,2-trichloroethylacetal,
  piperazine-1,4-diylbis-(1-(2,2,2-trichloroethyl)-formamide),
  1-(3,4-dichloroanilino)-1-formylamino-2,2,2-trichloroethane,
  2,6-dimethyl-N-tridecylmorpholine and its salts,
  2,6-dimethyl-N-cyclododecylmorpholine and its salts,
  N-[3-(p-tert.-butylphenyl)-2-methylpropyl]-cis-2,6-dimethylmorpholine,
  N-[3-(p-tert.-butylphenyl)-2-methylpropyl]-piperidine,
  1-[2-(2,4-dichlorophenyl)-4-ethyl-1,3-dioxolan-2-dioxolan-2-ylethyl]-1H-1,2,4-triazole,
  1-[2-(2,4-dichlorophenyl)-4-n-propyl-1,3-dioxolan-2-ylethyl]-1H-1,2,4-triazole,
  N-(n-propyl)-N-(2,4,6-trichlorophenoxyethyl)-N'-imidazolyl-urea,
  1-(4-chlorophenoxy)-3,3-dimethyl-1-(1H-1,2,4-triazol-1-yl)-butan-2-one,
  1-(4-chlorophenoxy)-3,3-dimethyl-1-(1H-1,2,4-triazol-1-yl)-butan-2-ol,
  1-(4-phenylphenoxy)-3,3-dimethyl-1-(1H-1,2,4-triazol-1-yl)-2-butanol,
  $\alpha$-(2-chlorophenyl)-$\alpha$-(4-chlorophenyl)-5-pyrimidinemethanol,
  5-butyl-(2-dimethylamino-4-hydroxy-6-methylpyrimidine,
  bis-(p-chlorophenyl)-3-pyridinemethanol,
  1,2-bis-(3-ethoxycarbonyl-2-thioureido)-benzene,
  1,2-bis-(3-methoxycarbonyl-2-thioureido)-benzene,
  and various fungicides, such as
  dodecylguanidine acetate,
  3-[3-(3,5-dimethyl-2-oxycylohexyl)-2-hydroxyethyl]-glutaramide, hexachlorobenzene,
  DL-methyl-N-(2,6-dimethylphenyl)-N-fur-2-yl alanate,
  methyl DL-N-(2,6-dimethylphenyl)-N-(2'-methoxyacetyl)-alanate,
  N-(2,6-dimethylphenyl)-N-chloroacetyl-DL-2-aminobutyrolactone,
  methyl DL-N-(2,6-dimethylphenyl)-N-(phenylacetyl)-alanate,
  5-methyl-5-vinyl-3-(3,5-dichlorophenyl)-2,4-dioxo-1,3-oxazolidine,
  3-[3,5-dichlorophenyl]-5-methoxymethyl-1,3-oxazolidine-2,4-dione,
  3-(3,5-dichlorophenyl)-1-isopropylcarbamylhydantoin,
  N-(3,5-dichlorophenyl)-1,2-dimethylcyclopropane-1,2-dicarboximide,
  2-cyano-[N-(ethylaminocarbonyl)-2-methoximino]-acetamide,
  1-[2-(2,4-dichlorophenyl)-pentyl]-1H-1,2,4-triazole,
  2,4-difluoro-$\alpha$-(1H-1,2,4-triazol-1-ylmethyl)-benzhydryl alcohol,
  N-(3-chloro-2,6-dinitro-4-trifluoromethylphenyl)-5-trifluoromethyl-3-chloro-2-aminopyridine, and
  1-((bis-(4-fluorophenyl)-methylsilyl)-methyl)-1H-1,2,4-triazole.

We claim:
1. Guanidiniumdodecylbenzene sulfonates of the formula I:

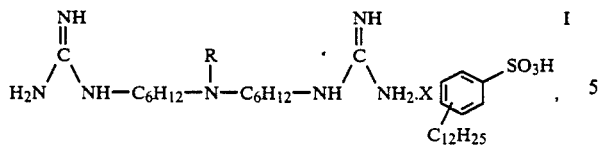

where
R is the group —H, —CH$_3$ or

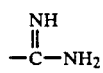

and
X is 1, 2, 3 or 4.

2. A fungicide containing a solid or liquid carrier and a fungicidally effective amount of a guanidiniumdodecylbenzene sulfonate of the formula I:

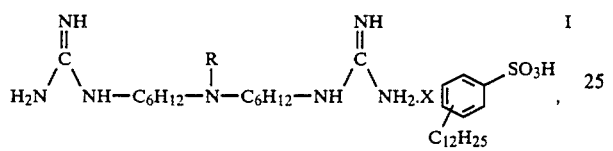

where
R is the group —H, —CH$_3$ or

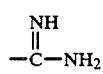

and
X is 1, 2, 3 or 4.

3. A process for combating fungi, wherein the fungi, or the materials, plants, seeds or the soil are treated with an effective amount of a guanidiniumdodecylbenzene sulfonate of the formula I:

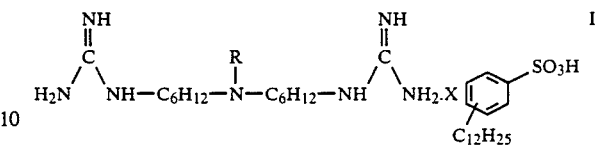

where
R is the group —H, —CH$_3$ or

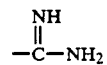

and
X is 1, 2, 3 or 4.

4. N,N''''-(Iminodi-6,1-hexanediyl)-bis-guanidine-tris-dodecylbenzene sulfonate.

5. N,N'''-Bis-[6-(aminoiminomethyl)-amino]-hexyl-guanidine-tris-dodecylbenzene sulfonate.

6. The guanidiniumdodecylbenzene sulfonates of claim 1, wherein X has a value of 3.

7. The fungicide of claim 2, wherein X has a value of 3.

8. The fungicide of claim 2, wherein said guanidiniumdodecylbenzene sulfonate comprises from 0.1 to 95% by wt. of the total weight.

9. The process of claim 3, wherein at least 0.02 kg of guanidiniumdodecylbenzene sulfonate is applied per hectare.

10. The fungicide of claim 2, which further comprises one of more other fungicidal substances.

* * * * *